· US007513874B2

United States Patent
Casset

(10) Patent No.: US 7,513,874 B2
(45) Date of Patent: Apr. 7, 2009

(54) DETERMINATION OF AN AVERAGE HEMODYNAMIC INDEX FOR AN ACTIVE IMPLANTABLE MEDICAL DEVICE SUCH AS CARDIAC PACEMAKER, DEFIBRILLATOR, CARDIOVERTOR AND/OR MULTISITE DEVICE

(75) Inventor: Cyrille Casset, Paris (FR)

(73) Assignee: ELA Medical S.A.S., Montrouge (FR)

( * ) Notice: Subject to any disclaimer, the term of this patent is extended or adjusted under 35 U.S.C. 154(b) by 1240 days.

(21) Appl. No.: 10/678,373

(22) Filed: Oct. 3, 2003

(65) Prior Publication Data

US 2004/0127944 A1    Jul. 1, 2004

(30) Foreign Application Priority Data

Oct. 4, 2002    (FR) ................... 02 12290

(51) Int. Cl.
A61B 5/02    (2006.01)
(52) U.S. Cl. .................................... 600/508
(58) Field of Classification Search ............ 607/28; 600/508, 547
See application file for complete search history.

(56) References Cited

U.S. PATENT DOCUMENTS

2001/0012953 A1*  8/2001  Molin et al. ............... 607/9
2001/0021864 A1   9/2001  Molin ....................... 607/17
2001/0034540 A1* 10/2001  Molin ....................... 607/20

FOREIGN PATENT DOCUMENTS

EP    1 116 497    1/2001
EP    1 138 346    3/2001

* cited by examiner

Primary Examiner—Mark W Bockelman
Assistant Examiner—Eric D Bertram
(74) Attorney, Agent, or Firm—Orrick Herrington & Sutcliffe, LLP

(57) ABSTRACT

An active implantable medical device such as a cardiac pacemaker, defibrillator, cardiovertor and/or multisite device that is able to determine and average a hemodynamic index parameter. The intracardiac impedance signal is correlated to the instantaneous blood flow, and is used to determine periodically an average hemodynamic index ($D_{ave}$) evaluated over several cardiac cycles under certain preset measurement conditions. For example, the preset conditions include checking that the state of the patient and of the device satisfies, the criteria (stages 12-20) defining predetermined measurement conditions, and inhibiting the determination of the aforesaid hemodynamic index if these criteria are not satisfied. A plurality of samples ($Z_{ij}$) of the measured impedance signal are collected over a length of time ($T_i$) of the systole of one cardiac cycle. Using the aforesaid samples, a value ($D_i$) representative of the blood volume ejected throughout this systole is determined by integrating the samples over the time period. Then, average hemodynamic index ($D_{ave}$) is calculated from a plurality of such integrated sample values successively determined over a plurality ($N_2$) of cardiac cycles.

9 Claims, 2 Drawing Sheets

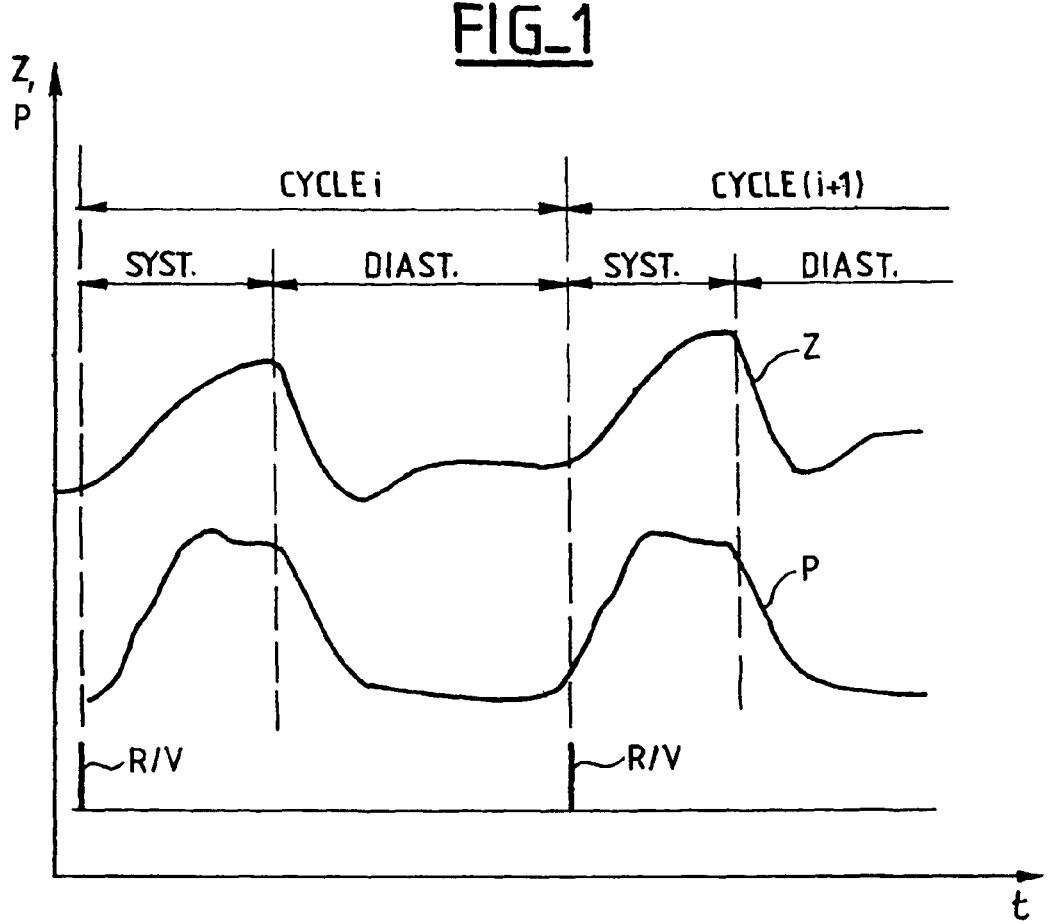
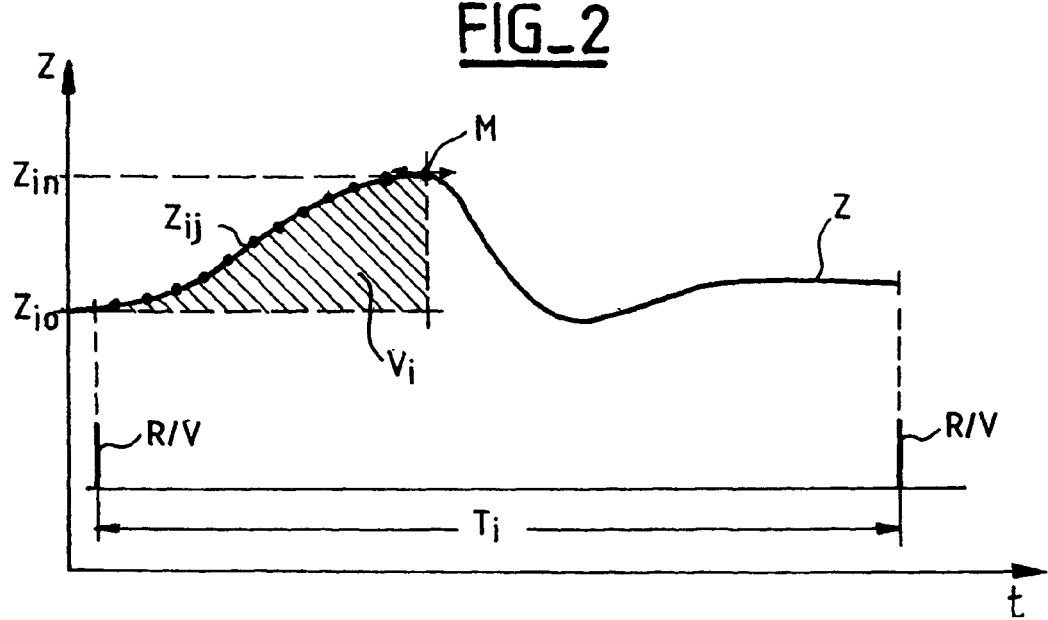

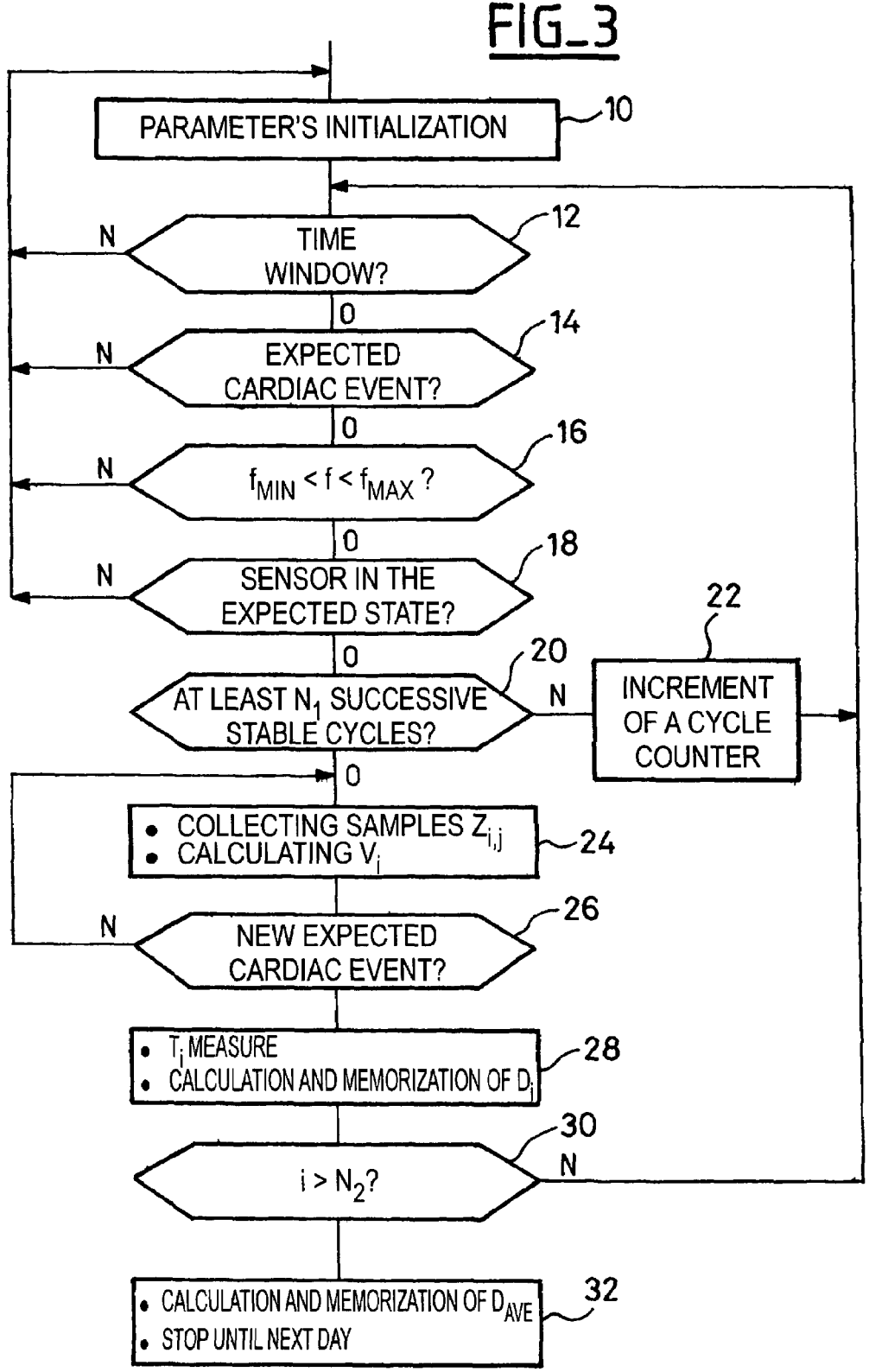

US 7,513,874 B2

DETERMINATION OF AN AVERAGE HEMODYNAMIC INDEX FOR AN ACTIVE IMPLANTABLE MEDICAL DEVICE SUCH AS CARDIAC PACEMAKER, DEFIBRILLATOR, CARDIOVERTOR AND/OR MULTISITE DEVICE

FIELD OF THE INVENTION

The present invention relates to "active implantable medical devices" as such devices are defined by the Jun. 20, 1990 directive 90/385/CEE of the Council of the European Communities, and more particularly to cardiac pacemaker, defibrillator and/or cardiovertor devices that are able to deliver to the heart stimulation pulses of low energy for the treatment of cardiac rhythm disorders. The present invention more advantageously concerns "multisite" prostheses in which electrodes are placed in a plurality of distinct cardiac sites comprising at least one ventricular site and one atrial site. This includes, for example, a prosthesis of the "double chamber" (right atrial stimulation and right ventricular stimulation), "triple chamber" (right atrial stimulation and double ventricular stimulation), and "quadruple chamber" (double atrial stimulation and double ventricular stimulation) types.

BACKGROUND OF THE INVENTION

Controlling the stimulation implies making permanent an adjustment of various parameters such as the frequency of stimulation, the atrio-ventricular delay (AVD), and the interventricular delay in the case of a biventricular stimulation. These various parameters are adjusted according to signals delivered by a sensor, for example, a sensor of the ventilation-minute (MV), which is a physiological parameter used as a factor representative of the instantaneous metabolic needs (also referred to as cardiac output requirements) of the patient. Sensors that measure a physical characteristic such as movement via piezoelectric transducers, also are known.

Another factor that can be desirable to know is the cardiac flow. This is because it is possible, particularly with a multi-site pacemaker, to obtain an indication of the cardiac flow, and thus of the fraction of ejection. The latter is the hemodynamic reference parameter that is used to optimize the stimulation on the various sites.

The published EP-A-1 116 497 and its corresponding U.S. Pat. No. 6,604,002 B1, commonly assigned herewith to ELA Médical, describes a manner of taking a dynamic measurement of bio-impedance allowing for an evaluation of diastolic and systolic volumes, and thus obtaining an indication of the cardiac flow and the ejection fraction. The signal obtained can be used to control (i.e., modify) the heart rate and/or the atrio-ventricular delay in a direction that will obtain a maximization of the cardiac flow. It is also possible to use the parameter thus measured to control the interventricular delay, in the case of a biventricular stimulation.

In addition, and more particularly, this prior art document describes a measurement technique for measuring the bio transvalvular impedance (i.e., the impedance between the atrium and the ventricle located on the same side of the heart) by a tripolar configuration, with injection of a current pulse between an atrial site and a ventricular site, and the collection (detection) of a differential potential between an atrial site and a ventricular site, with one of the sites being common to the injection and the collection, and with one site being specific for the injection and one site specific for the collection. The injected current pulse is a current of low amplitude, that is an amplitude that is insufficient to excite the cardiac cells or initiate a depolarization.

The published EP-A-1 138 346 and its corresponding U.S. Published Patent Application No. US 2001-0034540 A1 (published on 29 Oct. 2001), now U.S. Pat. No. 6,725,091, also commonly assigned herewith to ELA Medical, describes another type of measurement of the bio impedance, namely, a trans-septum bio-impedance, i.e., between one site located on one side of the heart and a second site located on the other side of the heart. Through this technique, one can obtain a value representative of the ejection fraction, although the bio-impedance signal is weaker than in the case of the transvalvular bio-impedance measurement, and also is more influenced by the impedance of the septum tissues.

OBJECTS AND SUMMARY OF THE INVENTION

It is, therefore, an object of the present invention to measure an intracardiac impedance and determine, under pre-established, standardized conditions, an index that is representative of the evolution of the cardiac flow of the patient over the long term. It is further object to measure this index (hereafter to be called the "average hemodynamic index") at regular intervals, for example, daily, such that the indices can be memorized (i.e., stored in memory) in the device for later use by a physician or other therapist for diagnostic purposes.

Advantageously, it has been discovered by the inventors that, under the strict conditions of time, the heartbeat rate and the state of the sensor incorporated in the device, the daily variations of the average hemodynamic index that can be obtained by the measurement of intracardiac bio-impedance are representative of the evolution of the state of the right heart of the patient. These variations also reflect, in an indirect way, what occurs in the lungs, on the left heart and the oxygenated tissues of the patient, because of the general repercussion on the whole body of the blood flowing in the right heart. Thus, in the case of a double chamber pacemaker, if the evolution of the average hemodynamic index reveals a deterioration of the hemodynamic state of the patient, but the cardiac activity remains satisfactory, then the physician will be able to suspect a pulmonary insufficiency.

The present invention also makes it possible to establish an earlier diagnosis of the cardiac insufficiency and/or to carry out comparisons of the hemodynamic state of the patient under recurring and well defined conditions with a suitable modification of the operating mode of the device. One can thus plan, if the patient does not present a significant cardiac disorder, to carry out daily measurements of bio-impedance during one week in a stimulated mode, then during another week in a non stimulated mode (while letting the spontaneous natural rate express), and then to compare the two series of measurements in order to evaluate the relevance and the effectiveness of making the stimulation permanent.

To this end, the present invention broadly is dedicated to a device of the general known type according to the EP-A-1 116 497 and its corresponding U.S. Pat. No. 6,604,002 B1 mentioned above, including at least one ventricular site and one atrial site, and means for determining a signal of intracardiac impedance correlated to the instantaneous blood flow, these means operating by injection of a current and collection of a differential potential on respective terminals of a configuration of the aforesaid sites. The U.S. Pat. No. 6,604,002 B1 is incorporated by reference herein in its entirety.

According to the invention, this device further includes means for processing the acquired or measured impedance signal and determining periodically an average hemodynamic index, the index being based on the impedance measurements evaluated over several cycles under preset measurement conditions. Preferably the foregoing means include: control means for checking that the state of the patient and of the device fulfills certain criteria defining the predetermined measurement conditions, and to inhibit the determination of the index if these criteria are not satisfied; measuring means for collecting a plurality of samples of the measured impedance signal throughout the systole of a cardiac cycle; integrating means for determining from the plurality of impedance samples a value representative of the blood volume ejected throughout the systole; and calculating means for establishing the aforementioned average hemodynamic index based upon a plurality of the aforesaid impedance values successively determined by the integrating means over a plurality of cardiac cycles.

Advantageously, the measuring means include a means for determining the moment a systole begins by detection of a predetermined ventricular cardiac event, and for determining the end of this same systole when the impedance signal reaches a maximum during the same cardiac cycle. The integrating means is in particular able to include a means for determining the value representative of the blood volume ejected by an evaluation of the increase in the resultant integrated value, i.e., the determined (actual or approximated) area under the curve defined by the plot of the measured impedance signal between the beginning and the end of the systole.

The calculating means can preferably include means for determining the hemodynamic index by calculating an average of the successive values of the representative hemodynamic index values for each systole, weighted by the duration of the systole associated with each index value.

Preferably, the means for delivering the intracardiac impedance signal comprise means for delivering a transvalvular impedance signal, operating by injection of a current between an atrial site and a ventricular site located on the same side of the heart and collection of a differential potential between an atrial site and a ventricular site also located on the same side of the heart. The control means can in particular include means for checking:

1. That the current time is located inside a predetermined temporal window;
2. That the ventricular event and the atrial event associated with the current cardiac cycle form a couple of events of an expected predetermined type;
3. That the heart rate associated with the current cycle is included between a first predetermined limits and a second predetermined limit;
4. That a sensor for controlling the device indicates a predetermined state of the patient; and/or
5. That a predetermined number of preceding cardiac cycles for which the state of the patient and of the device fulfilled the predetermined of criteria have occurred.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1 illustrates a chronogram giving the evolution, during two successive cardiac cycles, of the cardiac intraventricular pressure and the bio-transvalvular impedance;

FIG. 2 illustrates a chronogram showing the way in which the bio-impedance evolves during a cardiac cycle, and in which one performs various samplings and measurements necessary to the implementation of the invention; and FIG. 3 is a flow chart clarifying the various stages of the implementation of the invention.

DETAILED DESCRIPTION OF THE INVENTION

With reference to FIG. 1, the characteristic reference P illustrates the evolution over time t of the cardiac pressure in the right ventricle, with the succession of the systolic (Syst.) and diastolic (Diast.) phases in the cardiac cycle.

During the systole (Syst.), the pressure P increases quickly, then is stabilized in the neighborhood of a maximum value, having a characteristic plateau corresponding to the beginning of the opening of the valves. The cavities are then emptied throughout the diastole (Diast.) phase, until the following ventricular event, spontaneous (event R) or stimulated (event V) (collectively indicated as "R/V"). The duration of a cardiac cycle will be defined as the interval of time separating two spontaneous or stimulated successive ventricular events (also known as a coupling interval).

Also with reference to FIG. 1, the intracardiac impedance Z are illustrated. In this example, the transvalvular impedance Z (preferably selected over a trans-septal impedance, for the reasons indicated above), can be seen to have variations that closely correlated with the variations of the cardiac pressure P. In particular, the characteristic of transvalvular impedance presents a maximum corresponding precisely to the end of the ventricular systole, which thus can be easily detected (the end of the ventricular systole corresponding to the state of maximum contraction of the ventricle and, therefore, with the situation where blood volume is lowest, and consequently with a high value of the transvalvular impedance).

With reference to FIG. 2, which illustrates the variation of the transvalvular impedance Z during a cardiac cycle of duration $T_i$ defined, as indicated above, as being the interval of time separating two ventricular events (R or V) is illustrated. Here, the invention proposes to evaluate the volume ejected during the systolic phase of this "ith" cycle, starting from the variation of impedance Z.

This volume is generally proportional to the area $V_i$ is shown in hatched marks in FIG. 2, i.e., with the increase in the region located under the impedance curve Z, this increase being counted between, on the one hand, the beginning of the cardiac cycle (when the device detects the occurrence of the ventricular event R or V) and, on the other hand, the end of the systole, detected by the change of the direction of variation of the impedance curve Z (maximum M) (an inflection point).

Region $V_i$ could be evaluated by integration of signal Z starting from successive samples $Z_{ij}$ collected between the moment of beginning of the cardiac cycle ($Z_{i0}$ sample) ($Z_{ij}$, where j=0) and the point where the curve of impedance reaches its maximum ($Z_{in}$ sample) ($Z_{ij}$, where j=n).

The volume $V_i$ and the duration $T_i$ of the associated cycle will thus make it possible to calculate, in the manner that one will indicate below, a hemodynamic index $D_i$ associated with this "ith" cycle. This process, repeated for a predetermined number of cycles, will make it possible to obtain an hemodynamic index average $D_{ave}$ which will be then memorized (stored in memory) in the apparatus for later downloading by telemetry and use by the physician or by a suitable software analysis.

The flow chart of FIG. 3 illustrates the various stages of the implementation of the invention. As indicated above, the objective is to seek to determine a hemodynamic index value under recurring and well defined conditions, and preferably at regular intervals (for example, daily), so as then to be able to evaluate the evolution of the hemodynamic index value over the long term. It is, therefore, necessary before any measurement is made to check that all of the particular conditions are satisfied and maintained throughout the measurement.

After initialization of the various parameters of the algorithm (stage 10), one determines first of all whether the current hour corresponds to the predetermined time window during which the measurement must be taken (stage 12). One can, for example, program the device so that this measurement is carried out in a phase where one is about certain that the patient will be at rest, and in a comparable physiological state from one day to the next. This can be achieved, for example, by defining a time window that is between midnight and three o'clock in the morning. If this first criterion is verified, the algorithm next examines whether an expected cardiac event, such as a ventricular event, is detected (stage 14).

Indeed, insofar as a stimulation pulse modifies the hemodynamic condition of the patient, the rate must be of the same nature for all the cycles over which the measurement is made. This parameter can be selected among four possible rates, defined by pairs of predetermined events: P-R, P-V, A-R or A-V (P and A indicating respectively the spontaneous and stimulated atrial events, and R and V respectively indicating the spontaneous and stimulated ventricular events).

Next, the algorithm examines whether the frequency f of the rate of heartbeat (cardiac rhythm) is between two predetermined limits $f_{min}$ and $f_{max}$, between which the running cycle can be regarded as exploitable for purposes of the calculation of the hemodynamic index (stage 16). For example, one defines that the frequency f must be included between 60 and 65 bpm, or between 60 and 70 bpm, or any other relatively narrow range of values, a function of the patient's physiology.

The following stage (stage 18) is directed to checking whether the device is equipped with one or more sensors in a predetermined state, for example, a state defining a phase of rest. The algorithm then checks (stage 20) that the various criteria that have been satisfied (stages 12, 14, 16, 18) were all cumulatively checked during a $N_1$ number of successive cardiac cycles, for example $N_1=10$ successive cycles. In the contrary case, a cycle counter $N_1$ is incremented (stage 22) and the steps of stages 12 to 18 are reiterated until $N_i > N_1$.

When the criteria of stability exists for at least $N_1$ successive cycles, the device is ready to begin the recording the impedance and the processing of the values that will be recorded.

The first stage of this measurement phase concerns collecting the $Z_{ij}$ samples of impedance and integrating the value for each ith cycle, i.e. of the impedance curve so as to determine a region, defined above as $V_i$, with reference to FIG. 2 (stage 24), until detection of the maximum M. The algorithm then awaits the following cardiac event by checking (stage 26) that it corresponds to the type of preset rate (e.g., P-R, P-V, A-R or A-V). In the negative case, the measurement is not preserved, and is started again with the following cycle.

In the affirmative case, the algorithm determines the duration $T_i$ of the cardiac cycle which has just finished, and deduces the hemodynamic index $D_i$ corresponding to this cycle (stage 28). This $D_i$ index is given as being the $D_i$ quotient=$V_i/T_i$ of ejected volume $V_i$ by the duration of the cycle $T_i$. If it is indeed necessary to know the real hemodynamic state of the patient, the ejected volume during a cycle can be weighted by the duration of the cycle, the best hemodynamic state corresponding to a large ejected volume during a cycle of short duration. The hemodynamic index $D_i$ is thus determined for a plurality of a number $N_2$ of successive cycles, for example, over $N_2=10$ successive cycles (stage 30).

Once this series of measurements is completed, the algorithm then calculates (stage 32) the hemodynamic value of the index average $D_{ave}$, which is the arithmetic mean of the $D_i$ indices over the considered $N_2$ cycles. This daily hemodynamic index average is then memorized, which puts an end to the process until the next day (i.e., the next time window (stage 12).

Suitable devices for which the present invention has application include, for example, the active implantable medical devices available from Ela Médical, Montrouge France. These devices are microprocessor-based systems having circuits for receiving, conditioning and processing detected electrical signals, and capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricle, in the left and/or right chambers, are well known and any suitable design may be used. The circuits used to inject the currents to obtain the bioimpedance measurements are known as well from, for example, EP 1 116 497 and corresponding U.S. Pat. No. 6,604,002 B1 and EP 1 138 346 and corresponding U.S. Published Pat. Application 2001-0034540, now U.S. Pat. No. 6,725,091, and any suitable circuit to may be used. The sensor used and the determination of rest phases might be taken from the devices disclosed in, for example, U.S. Pat. No. 5,722,996 and EP1317943 and its corresponding U.S. Published Patent Application 2002-10310689, which disclosures are incorporated herein by reference. The use of an MV type sensor to determine when a patient is in a rest phase or state is described in U.S. Pat. No. 5,622,428, which is incorporated herein by reference.

One skilled in the art will appreciate that the present invention can be practiced by other than the described embodiments, which are presented for purposes of illustration and not of limitation.

I claim:

1. An active implantable medical device, in particular a cardiac pacemaker, defibrillator, cardiovertor and/or multi-site device, having at least one electrode terminal placed in each of at least two distinct respective sites including at least one ventricular site and one atrial site, comprising:

means for measuring an intracardiac impedance signal correlated to an instantaneous blood flow, said means comprising a pulse generator providing a current injection and circuit for collecting a differential potential across said respective electrode terminals in response to said current injection; and means for determining periodically, in response to said measured impedance signal, an average hemodynamic index evaluated over a number of successive cardiac cycles satisfying a plurality of preset measurement conditions, said means including:

control means for checking a state of the patient and criteria corresponding to a set of predetermined measurement conditions and for inhibiting the determination of said average hemodynamic index if said criteria set are not satisfied;

measuring means for determining a plurality of the measured impedance signal samples over a first duration corresponding to a systole of one cardiac cycle, further comprising means for determining a beginning of a systole by detection of a predetermined ventricular cardiac event, and determining an end of said same systole in response to said impedance signal reaching a maximum during said same cardiac cycle;

integrating means for determining, in response to said determined samples, a value representative of a blood volume ejected throughout said systole;

calculating means for establishing said average hemodynamic index in response to a plurality of said values successively determined by the integrating means over a plurality of cardiac cycles.

2. The device of claim 1, wherein the integrating means further comprises means for determining said value representative of the ejected blood volume in response to an evaluation of an increase in an area of the measured impedance signal between said determined beginning and end of the systole.

3. The device of claim 1, wherein the calculating means further comprises means for weighting each determined value as a function of the duration over which said value was determined, and said plurality of weighted representative values over said plurality of successively determined values.

4. The device of claim 1, wherein the means for measuring the intracardiac impedance signal further comprises means for delivering a transvalvular impedance signal, said electrode terminals and said pulse generator being configured to inject said injection current between an atrial site and a ventricular site located on the same side of the heart, and said collecting circuit being configured to collect a differential potential between an atrial site and a ventricular site also located on said same side of the heart.

5. The device of the claim 1, wherein one of said predetermined measurement conditions further comprises a current hour being located inside a predetermined temporal window.

6. The device of claim 1, wherein one of the predetermined measurement conditions further comprises a detected ventricular event and a detected atrial event being associated with a current cardiac cycle and forming a pair of predetermined events.

7. The device of the claim 1, wherein one of the predetermined measurement conditions further comprises a detected heart rate associated with the current cycle being between a minimum predetermined limit and a maximum predetermined limit.

8. The device of the claim 1, wherein the control means further comprises a sensor having an output indicative of a patient state, the state checking means further comprising means for checking whether said activity sensor output corresponds to said predetermined state of the patient.

9. The device of claim 1, wherein one of the predetermined measurement conditions further comprises a predetermined number of consecutive preceding cardiac cycles during which the state of the patient and of the device have satisfied said criteria.

* * * * *